United States Patent [19]

Pering

[11] 4,116,229
[45] Sep. 26, 1978

[54] ACOUSTIC IMAGING APPARATUS

[75] Inventor: Richard D. Pering, Palo Alto, Calif.

[73] Assignee: Hewlett-Packard Company, Palo Alto, Calif.

[21] Appl. No.: 718,721

[22] Filed: Aug. 30, 1976

[51] Int. Cl.² .............................................. A61B 10/00
[52] U.S. Cl. ..................................... 128/2 V; 73/626; 340/1 R
[58] Field of Search ............... 128/2 V, 24 A, 2.05 Z; 340/5 H, 6 R, 5 MP, 1 R; 333/30 R, 70 R, 70; 73/67.9, 71.5 US, 609, 617, 625, 628, 626, 67.5 H, 67.8 S

[56] References Cited

U.S. PATENT DOCUMENTS

| 3,869,693 | 3/1975 | Jones | 340/6 R |
|---|---|---|---|
| 3,918,024 | 11/1975 | Macovski | 340/5 MP |
| 4,005,382 | 1/1977 | Beaver | 340/6 R |
| 4,058,003 | 11/1977 | Macovski | 128/2 V |

Primary Examiner—Robert W. Michell
Assistant Examiner—Francis J. Jaworski
Attorney, Agent, or Firm—Donald N. Timbie

[57] ABSTRACT

An array of transducers is focussed by insertion of a means for providing a small variable delay between each transducer and a selected tap on a master delay line.

3 Claims, 1 Drawing Figure

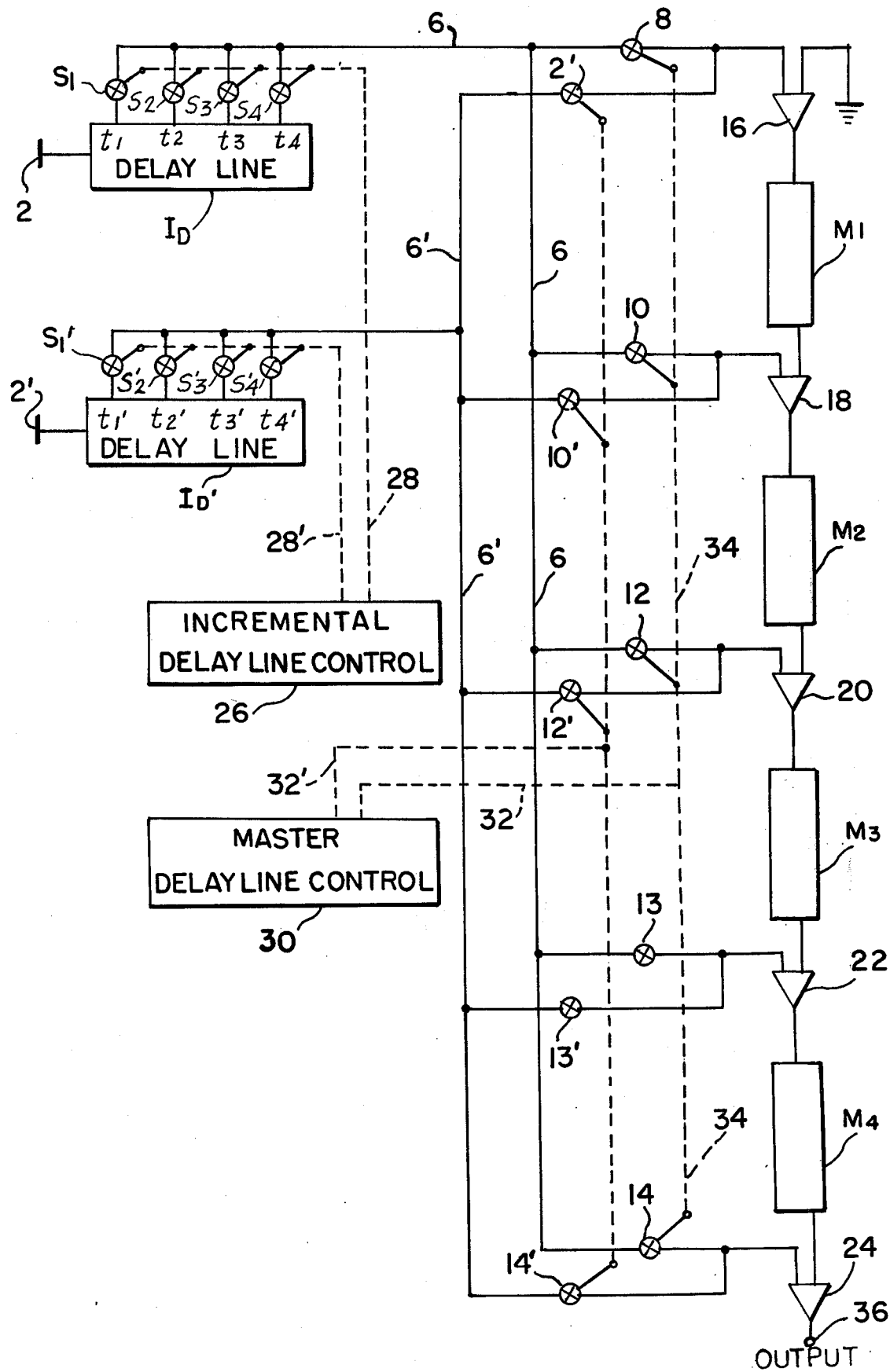

ACOUSTIC IMAGING APPARATUS

BACKGROUND OF THE INVENTION

Much attention has been given in recent years to the development of ultrasonic systems for producing real time images of internal portions of the human body. In one system an array of transducers for converting short pulses of alternating current electrical waves into corresponding pressure waves is placed in contact with the body. By choosing the relative times of application of the pulses of electrical waves to the transducers, the pressure wave for each pulse can be formed into a beam extending in any desired direction. The direction of the beam of pressure waves for each pulse can be changed so as to effectively scan a sector. As the pulses of pressure waves pass through the body tissue, a portion of their energy is reflected whenever they encounter tissue having a different acoustic characteristic. An array of receiving transducers that convert the reflected pressure waves into corresponding electrical waves is dynamically focused (from a minimum to a maximum range) along the direction of each transmitted beam.

Focusing of the array of receiving elements at a given point requires that the few cycles of the alternating current wave derived by each of the transducers from the pulses of pressure waves reflected from that point be superimposed in phase at a summing point. This produces a strong signal, whereas reflections of pressure waves from other points produce electrical waves that reach the summing point with random phase relationships. Because the distances between any desired focal point and the various receiving transducers are usually different, the reflections arrive at the transducers at different times. It is therefore necessary to introduce compensating delays between each transducer and the summing point so that the total time between reflection of a pressure wave at the focal point and the arrival of the corresponding electrical wave at the summing point is the same regardless of which transducer is involved. The compensating delays are varied dynamically so that the focal point moves from minimum to maximum range along each direction of the transmitted pulses as previously described.

In some previous instruments, for example, separate tapped delay lines have been connected to each transducer and the delay required for focusing is determined by connecting an appropriate tap to the summing point. Each delay line must be capable of providing the maximum amount of delay required by the transducer to which it is connected, so that the sum of the delays for all the delay lines is large. Inasmuch as each line has a high individual cost, an instrument constructed in this manner is necessarily expensive.

This invention basically involves using one long delay line, the master line, that is effectively tapped so that a signal injected into each tap experiences a different delay. A plurality of incremental delay means having small variable delays are provided. Each is connected between one or more of the transducers and a selected tap on the master line. The small variable delay can be provided by any means known to those skilled in the art, e.g., a line of lumped inductances and/or capacitors with either or both variable, means for combining delay lines of small but different delays by switched interconnections, and by a simple tapped short delay line. In the description that follows the small or variable delays are provided by a tapped delay line, but other equivalent controllable incremental delay means may be used.

The taps on the master delay line to which the transducers are connected through the small variable delays are selected so as to focus the array along a desired scan angle or direction and the small variable delays are changed during a scanning of that direction so as to shift the focus of the array from minimum to maximum range.

The drawing shows a preferred embodiment of the transducer array with associated variable delay elements and selective interconnection into the master delay line.

In the drawing, a transducer 2 or other signal source, is connected to one end of an incremental delay line $I_d$ having a plurality of taps $T_1$, $T_2$, $T_3$, and $T_4$ thereon. Incremental delay line tap controlling switches $S_1$, $S_2$, $S_3$, and $S_4$ are respectively connected between these taps and a bus 6. Master delay line tap controlling switches 8, 10, 12, 13 and 14 are respectively connected between the bus 6 and an input of summing amplifiers 16, 18, 20, 22 and 24. The master delay line is comprised of a plurality of sections, the section $M_1$ being connected between the output of the amplifier 16 and an input of the amplifier 18, the section $M_2$ being connected between the output of the amplifier 18 and an input of the amplifier 20, the section $M_3$ being connected between the output of the amplifier 20 and an input of the amplifier 22, and the section $M_4$ being connected between the output of the amplifier 22 and an input of the amplifier 24. Means, such as the incremental delay line control 26, are provided for selectively closing only one of the switches $S_1$ through $S_4$ for desired intervals by signals sent to the switches over a conductor represented by a dotted line 28, and means, such as the master delay line control 30, are provided for closing only one of the switches 8 through 14 for other desired intervals by signals sent to the switches over conductors represented by dotted lines 32 and 34. Thus the delay line $I_0$, the delay line control 26, the switches $S_1 - S_4$, the bus 6 and the switches 8 – 14 form a means for selectivly providing predetermined small amounts of incremental delay between each of said transducers and one of said taps on said master delay line.

It will be apparent to those skilled in the art that the bus 6 could be connected to one end of the incremental delay line $I_d$ and the transducer 2 connected to the various taps by the switches $S_1 - S_4$.

In an actual instrument a number of receiving transducers are used, but in the interest of simplicity only one other is shown. It, and the components corresponding to those just described are indicated by the same numerals or letters primed.

With the arrangement just described, the array of transducers including the transducers 2, 2' can be generally focused along a given direction by closing an appropriate master delay line tap control switch for each transducer. Thus for a particular direction one of the switches 8 – 14 and one of the switches 8' – 14' would be closed. The master delay line provides the minimum delay required for each transducer during the time the focal point of the array is to be at points along a given direction. Causing the focus of the array to progressively advance from minimum to maximum range along the chosen direction may be achieved by closing one o the incremental delay line tap controlling switches $S_1$ - $S_4$ for each transducer in an appropriate sequence.

The details of the control circuits 26 and 30 and the means for closing the various switches in a desired manner are not illustrated inasmuch as they would be well understood by those skilled in the art and do not, therefore, form part of this invention. It can be seen, however, that the difference in times of arrival of reflections of the ultrasonic waves from any focal point in the body can be compensated for by the system just described so that the alternating current electrical waves corresponding to these reflections will arrive in phase at the output terminal 36.

A great advantage of the invention is the nearly 80% reduction in the total amount of delay that is required. This arises from the fact that sections of the master delay line may provide a portion of the delay for more than one transducer.

What is claimed is:

1. In an apparatus for forming real time images of internal portions of the human body from reflections by internal tissue of transmitted short pulses of ultrasonic waves, the combination of
   an array of receiving transducers,
   a master delay line having a plurality of taps thereon and fixed delays between successive taps, and
   means for selectively providing predetermined small amounts of incremental delay between each of said transducers and any one of said taps on said master delay line.

2. Apparatus as set forth in claim 1 wherein said last named means is comprised
   a plurality of tapped incremental delay lines
   a bus
   means connecting one end of each of said delay lines and a selected tap thereon in series between said bus and one or more of said transducers, and
   means connecting said bus to any one of said taps on said master delay line.

3. In apparatus for scanning the focal point of an array within a range along a given direction with respect to the array, the combination of
   an array of transducers,
   a master delay line having a plurality of taps thereon and an output terminal, there being fixed delays between successive taps,
   a plurality of tapped incremental delay lines, each having an input and an output, the delay between the input and output being determined by the setting of a tap thereon,
   means for respectively connecting each of a plurality of transducers to the inputs of their respective incremental delay lines,
   means for respectively connecting the outputs of said incremental delay lines to selected taps on said master delay line, each tap having a delay between it and said output terminal equal to the minimum delay required by the transducer coupled to it via an incremental delay line when the transducer is focussed in said range, and
   means for changing a tap on each incremental delay line so as to provide the additional delay required to focus it at different points in said range.

* * * * *